(12) United States Patent
Domash et al.

(10) Patent No.: US 7,559,914 B2
(45) Date of Patent: Jul. 14, 2009

(54) PRIMING A MICROSURGICAL SYSTEM

(75) Inventors: David M. Domash, Irvine, CA (US);
Mark A. Hopkins, Mission Viejo, CA (US); John C. Huculak, Mission Viejo, CA (US); Nader Nazarifar, Laguna Niguel, CA (US)

(73) Assignee: Alcon, Inc., Hunenberg (CH)

( * ) Notice: Subject to any disclaimer, the term of this patent is extended or adjusted under 35 U.S.C. 154(b) by 101 days.

(21) Appl. No.: 11/549,785

(22) Filed: Oct. 16, 2006

(65) Prior Publication Data

US 2007/0135752 A1    Jun. 14, 2007

Related U.S. Application Data

(60) Provisional application No. 60/750,212, filed on Dec. 14, 2005.

(51) Int. Cl.
*A61M 1/00* (2006.01)

(52) U.S. Cl. ........................................ 604/30

(58) Field of Classification Search ............. 604/65–67, 604/30–35, 131, 132, 154, 156, 315; 128/DIG. 12, 128/DIG. 13
See application file for complete search history.

(56) References Cited

U.S. PATENT DOCUMENTS

| | | | |
|---|---|---|---|
| 4,293,413 | A | 10/1981 | Schnell |
| 5,041,215 | A | 8/1991 | Chamberlain, Jr. et al. |
| 5,249,121 | A | 9/1993 | Baum et al. |
| 5,281,112 | A | 1/1994 | Montoya et al. |
| 5,650,071 | A | 7/1997 | Brugger et al. |
| 5,910,110 | A | 6/1999 | Bastable |
| 6,168,561 | B1 | 1/2001 | Cantu et al. |
| 6,302,653 | B1 * | 10/2001 | Bryant et al. .................. 417/53 |

* cited by examiner

*Primary Examiner*—Manuel A Mendez
(74) *Attorney, Agent, or Firm*—W. David Lee

(57) ABSTRACT

A microsurgical system capable of priming its aspiration circuit using a pressurized gas source, a pressurized infusion fluid source, an aspiration chamber fluidly coupled to the pressurized gas source and the pressurized infusion fluid source, and a computer.

7 Claims, 1 Drawing Sheet

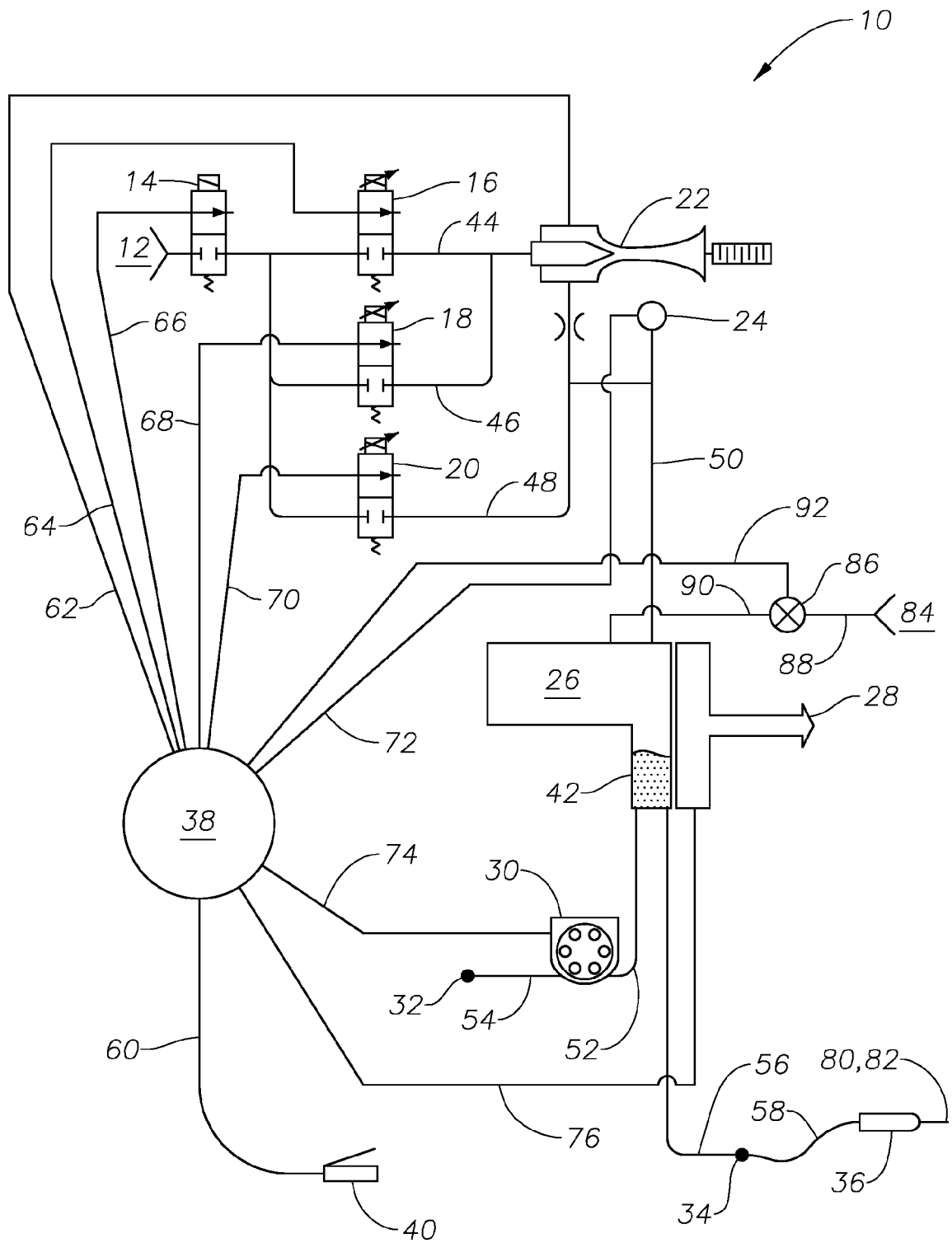

PRIMING A MICROSURGICAL SYSTEM

This application claims the priority of U.S. Provisional Application No. 60/750,212 filed Dec. 14, 2005.

FIELD OF THE INVENTION

The present invention generally pertains to priming an aspiration circuit of a microsurgical system and more particularly to priming the aspiration circuit of an ophthalmic microsurgical system.

DESCRIPTION OF THE RELATED ART

During small incision surgery, and particularly during ophthalmic surgery, small probes are inserted into the operative site to cut, remove, or otherwise manipulate tissue. During these surgical procedures, fluid is typically infused into the eye, and the infusion fluid and tissue are aspirated from the surgical site. Such probes are typically fluidly coupled to a microsurgical system via plastic tubing.

Priming the aspiration fluid paths of such microsurgical systems is typically done by aspirating an infusion fluid from a container in the sterile field. Such a process requires a user to manually fill a container with infusion fluid after priming the infusion circuit of the microsurgical system, immersing a probe into the container, and then instructing the surgical system to prime the aspiration circuit from the fluid in the container via the probe. As surgical probes have become smaller, aspirating the fluid through the small port of the probe has become more time consuming. In addition, this process becomes more complicated if an additional aspiration tool is needed after the surgical procedure has started. In this case, a second container of infusion fluid is required to prime the additional aspiration tool and its associated tubing. Such interruption of the surgical procedure is not desirable. This process may also require the use of the infusion circuit of the system. The use of the infusion circuit of the system to fill a second container, and the corresponding loss of infusion pressure into the eye, is even less desirable. Therefore, a need continues to exist for an improved method of priming an aspiration circuit of a microsurgical system.

SUMMARY OF THE INVENTION

The present invention provides improved apparatus and methods for priming an aspiration circuit of a microsurgical system. In one aspect of the present invention, a microsurgical system comprising a pressurized gas source, a pressurized infusion fluid source, an aspiration chamber fluidly coupled to the pressurized gas source and the pressurized infusion fluid source, and a surgical device having an aspiration port fluidly coupled to the aspiration chamber via a fluid line is provided. The aspiration chamber is filled with an amount of an infusion fluid from the pressurized infusion fluid source sufficient to substantially fill the fluid line and the surgical device. The aspiration chamber is pressurized with the pressurized gas source so that the infusion fluid substantially fills the fluid line and the surgical device.

BRIEF DESCRIPTION OF THE DRAWINGS

For a more complete understanding of the present invention, and for further objects and advantages thereof, reference is made to the following description taken in conjunction with the accompanying drawing, in which FIG. 1 is a schematic diagram illustrating an aspiration circuit of a microsurgical system.

DETAILED DESCRIPTION OF THE PREFERRED EMBODIMENTS

The preferred embodiment of the present invention and its advantages is best understood by referring to FIG. 1 of the drawings. Microsurgical system 10 preferably includes a pressurized gas source 12, an isolation valve 14, a vacuum proportional valve 16, an optional second vacuum proportional valve 18, a pressure proportional valve 20, a vacuum generator 22, a pressure transducer 24, an aspiration chamber 26, a fluid level sensor 28, a pump 30, a collection bag 32, an aspiration port 34, a surgical device 36, a computer or microprocessor 38, a proportional control device 40, a pressurized infusion fluid source 84, and an isolation valve 86. The various components of system 10 are fluidly coupled via fluid lines 44, 46, 48, 50, 52, 54, 56, 58, 88, and 90. The various components of system 10 are electrically coupled via interfaces 60, 62, 64, 66, 68, 70, 72, 74, 76, and 92.

Valves 14 and 86 are preferably an "on/off" solenoid valves. Valves 16-20 are preferably proportional solenoid valves. Vacuum generator 22 may be any suitable device for generating vacuum but is preferably a vacuum chip or a venturi chip that generates vacuum when isolation valve 14 and vacuum proportional valves 16 and/or 18 are open and gas from pressurized gas source 12 is passed through vacuum generator 22. Pressure transducer 24 may be any suitable device for directly or indirectly measuring pressure and vacuum. Fluid level sensor 28 may be any suitable device for measuring the level of a fluid 42 within aspiration chamber 26 but is preferably capable of measuring fluid levels in a continuous manner. Pump 30 may be any suitable device for generating vacuum but is preferably a peristaltic pump, a scroll pump, or a vane pump. Microprocessor 38 is capable of implementing feedback control, and preferably PID control. Proportional controller 40 may be any suitable device for proportionally controlling system 10 and/or surgical device 36 but is preferably a foot controller. Surgical device 36 may be any surgical device that aspirates tissue but is preferably an ophthalmic surgical device such as a phacoemulsification probe, a vitrectomy probe, or an aspiration probe. Surgical device 36 has a tip 80 with a port 82 that is fluidly coupled to fluid line 58. Fluid 42 may be any suitable infusion fluid, such as, by way of example, BSS PLUS® intraocular irrigating solution available from Alcon Laboratories, Inc. of Fort Worth, Tex. Fluid line 58 is preferably plastic tubing.

The following describes a preferred method of priming the aspiration circuit of FIG. 1 according to the present invention. Microprocessor 38 opens isolation valve 86 to supply fluid 42 to aspiration chamber 26 via pressurized infusion fluid source 84 and fluid lines 88 and 90. After a predetermined time, microprocessor 38 closes isolation valve 84, leaving aspiration chamber 26 containing sufficient fluid 42 to substantially fill fluid lines 56 and 58 and surgical device 36. Alternatively, fluid level sensor 28 may signal microprocessor 38 when a predetermined fluid level within aspiration chamber 26 is reached. Microprocessor 38 opens valves 14 and 20. Microprocessor 38 opens valve 20 for a sufficient time and degree so that pressurized air from pressurized air source 12 causes fluid 42 from aspiration chamber 26 to substantially fill fluid lines 56, 58, and surgical device 36, fully priming the aspiration circuit of system 10. Alternatively, fluid level sensor 28 may signal microprocessor 38 when a predetermined fluid level within aspiration chamber 26 is reached. Microprocessor 38 then closes valves 14 and 20. Some amount of fluid 42 remains in aspiration chamber 26, such as is shown in FIG. 1. Tip 80 of surgical device 36 is positioned in an upward direction so as to avoid passive flow of fluid 42 out of port 82.

From the above, it may be appreciated that the present invention provides significant advantages over the conventional method of priming the aspiration circuit of system 10 by placing port 82 of system 10 into a container of infusion fluid, as described hereinabove. First, the time required to fill the aspiration circuit of system 10 is significantly reduced, especially with a surgical device 36 having a small port 82. Second, the number of manual actions by a user is significantly reduced. Third, concurrent priming of the aspiration circuit and the infusion circuit of system 10 is possible. Fourth, when an additional aspiration tool is needed after a surgical procedure has begun, the additional aspiration tool may be primed without the infusion circuit of system 10. Thus, infusion pressure into the eye is not compromised.

The present invention is illustrated herein by example, and various modifications may be made by a person of ordinary skill in the art. For example, while the present invention is described above relative priming the aspiration circuit of an ophthalmic microsurgical system, it is also applicable to the aspiration circuits of other microsurgical systems.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. Apparatus for priming an aspiration circuit of a microsurgical system, comprising:
    a pressurized gas source;
    a pressurized infusion fluid source;
    an aspiration chamber fluidly coupled to said pressurized gas source and said pressurized infusion fluid source;
    a first valve fluidly coupled between said pressurized infusion fluid source and said aspiration chamber;
    a second valve fluidly coupled between said pressurized gas source and said aspiration chamber;
    a surgical device having an aspiration port fluidly coupled to said aspiration chamber via a fluid line;
    a computer electrically coupled to said first and second valves;
    whereby said computer:
        actuates said first valve so as to fill said aspiration chamber with an amount of an infusion fluid from said pressurized infusion fluid source sufficient to substantially fill said fluid line and said surgical device; and
        actuates said second valve so that pressurized gas from said pressurized gas source causes said infusion fluid in said aspiration chamber to substantially fill said fluid line and said surgical device.

2. The apparatus of claim 1 wherein said fluid line comprises plastic tubing.

3. The apparatus of claim 1 wherein said microsurgical system is an ophthalmic microsurgical system, and said surgical device is an ophthalmic surgical device.

4. The apparatus of claim 1 wherein said computer opens said first valve for a predetermined amount of time.

5. The apparatus of claim 1 further comprising a fluid level sensor operatively coupled to said aspiration chamber and electrically coupled to said computer, wherein said computer opens said first valve until said fluid level sensor signals said computer that a predetermined level of fluid is reached.

6. The apparatus of claim 1 wherein said computer opens said second valve for a predetermined amount of time.

7. The apparatus of claim 1 further comprising a fluid level sensor operatively coupled to said aspiration chamber and electrically coupled to said computer, wherein said computer opens said second valve until said fluid level sensor signals said computer that a predetermined level of fluid is reached.

* * * * *